United States Patent
Rodemerk et al.

(10) Patent No.: US 10,695,475 B2
(45) Date of Patent: Jun. 30, 2020

(54) PUMP ARRANGEMENT AND METHOD OF OPERATING A FLUID PUMP

(71) Applicant: Berlin Heart GmbH, Berlin (DE)

(72) Inventors: Aaron Rodemerk, Potsdam (DE); Adrian Wisniewski, Berlin (DE)

(73) Assignee: BERLIN HEART GMBH, Berlin (DE)

( * ) Notice: Subject to any disclaimer, the term of this patent is extended or adjusted under 35 U.S.C. 154(b) by 196 days.

(21) Appl. No.: 15/567,552

(22) PCT Filed: Apr. 20, 2016

(86) PCT No.: PCT/EP2016/058741
§ 371 (c)(1),
(2) Date: Oct. 18, 2017

(87) PCT Pub. No.: WO2016/173896
PCT Pub. Date: Nov. 3, 2016

(65) Prior Publication Data
US 2018/0110910 A1    Apr. 26, 2018

(30) Foreign Application Priority Data
Apr. 29, 2015   (EP) ..................... 15165567

(51) Int. Cl.
*A61M 1/10* (2006.01)
*A61M 1/12* (2006.01)

(52) U.S. Cl.
CPC ........ *A61M 1/1086* (2013.01); *A61M 1/1015* (2014.02); *A61M 1/1031* (2014.02);
(Continued)

(58) Field of Classification Search
CPC .............. A61M 1/1086; A61M 1/1015; A61M 1/1031; A61M 1/122; A61M 2205/3317;
(Continued)

(56) References Cited

U.S. PATENT DOCUMENTS

| 5,725,357 A | 3/1998 | Nakazeki et al. |
| 6,254,359 B1 | 7/2001 | Aber |

(Continued)

FOREIGN PATENT DOCUMENTS

| CN | 1407247 A | 4/2003 |
| CN | 101983732 A | 3/2011 |

(Continued)

*Primary Examiner* — Paula J Stice
(74) *Attorney, Agent, or Firm* — Brinks Gilson & Lione

(57) ABSTRACT

Methods for operating a liquid pump having a rotor are provided for conveying liquids. The viscosity of the conveyed liquid, such as blood, may be determined while taking into account measured values of operating parameters of the pump. The pump may be operated in a predetermined region of a family of characteristic curves. The family of characteristic curves may link at least two operating parameters of the pump to each other, and, in the predetermined region, at least three parameters of the pump may be sensed and taken into account in order to determine the viscosity. Because of the operation in a predetermined region of a family of characteristic curves, the viscosity of the conveyed liquid can be determined in addition to the volumetric flow rate through the pump and the pressure difference across the pump when an appropriate selection is made from a sufficient number of sensed operating parameters.

16 Claims, 2 Drawing Sheets

(52) U.S. Cl.
CPC ............. *A61M 1/122* (2014.02); *A61M 1/101* (2013.01); *A61M 2205/3317* (2013.01); *A61M 2205/3334* (2013.01); *A61M 2205/3344* (2013.01); *A61M 2205/3365* (2013.01); *A61M 2205/3368* (2013.01); *A61M 2205/8206* (2013.01); *A61M 2230/207* (2013.01)

(58) Field of Classification Search
CPC .. A61M 2205/3334; A61M 2205/3344; A61M 2205/3365; A61M 2205/3368; A61M 2205/8206; A61M 2230/207
See application file for complete search history.

(56) References Cited

U.S. PATENT DOCUMENTS

| | | |
|---|---|---|
| 6,512,677 B1 | 1/2003 | Bergherr et al. |
| 6,634,224 B1 | 10/2003 | Schöb et al. |
| 6,711,943 B1 | 3/2004 | Schöb |
| 2011/0137108 A1 | 6/2011 | LaRose et al. |
| 2014/0357937 A1 | 12/2014 | Reyes et al. |

FOREIGN PATENT DOCUMENTS

| | | |
|---|---|---|
| EP | 0 967 475 A1 | 12/1999 |
| EP | 0 971 212 A1 | 1/2000 |

PUMP ARRANGEMENT AND METHOD OF OPERATING A FLUID PUMP

CROSS-REFERENCE TO RELATED APPLICATIONS

This application is a 371 nationalization of international patent application PCT/EP2016/058741 filed Apr. 20, 2016, the entire contents of which are hereby incorporated by reference, which in turn claims priority under 35 USC § 119 to European patent application EP 15 165 567.7 filed on Apr. 29, 2015.

TECHNICAL FIELD

The invention is in the area of mechanical engineering and electrical engineering and can be used to special advantage in the area of medical technology. In particular, the invention relates to a pump for fluids in the medical field, particularly blood, wherein volumetric flow of the pump and/or a pressure differential generated by the pump are captured during operation.

DETAILED DESCRIPTION

Figure 1:
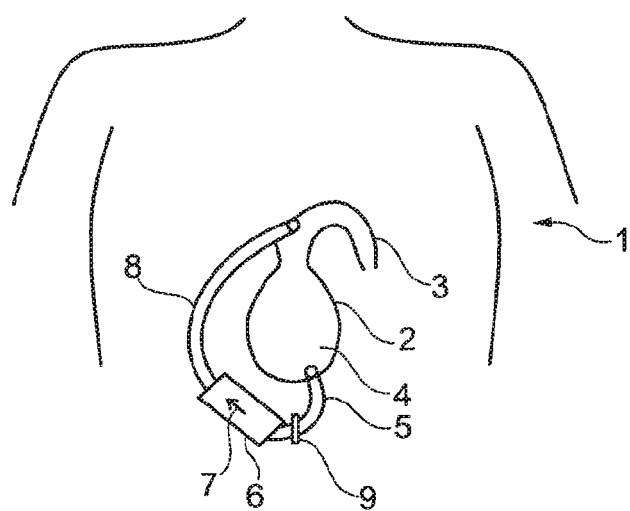
FIG. 1 schematically, a view of a patient's body with the heart of the patient and a VAD (ventricular assist device) pump.

In the medical field, fluid pumps are used for several purposes, on the one hand for conveying bodily fluids, particularly blood, and on the other hand, for conveying fluids foreign to the body, for example pharmacologically effective fluids supposed to be conveyed within, to, or from the body of a patient. Especially with regard to blood pumps, which convey blood within the patient's body or partly outside the patient's body and which are in particular employed as VAD (ventricular assist device) pumps, high demands are made on controlling and operation so as to be able to respectively measure and adjust a volumetric flow of the pump and/or a pressure differential with maximum accuracy and reliability.

With VAD blood pumps, which can convey the blood from the left ventricle into the aorta, for example, or with other blood pumps, for example RVAD pumps, volumetric flow can be determined on the basis of a map of characteristics of the pump from the rotating speed of a pump motor and the pressure differential across the pump. However, experience has shown that a map of characteristics, which usually links up the values of two or more operational parameters, is not usable with equal accuracy and reliability for the whole area of application of such a pump.

Here, several methods for determining volumetric flow of a pump or pressure differential from different sets of operational parameters are known in principle. Moreover, pressure differential across the pump and volumetric flow are not just determined by operational parameters of the pump, such as the rotating speed of a pump rotor and motor amperage of a motor driving the rotor, but are codetermined also by the viscosity of the fluid. Said viscosity is linked, for example, to temperature, and in the case of a bodily fluid also to physiological parameters such as e.g. hematocrit level.

In view of the prior art, it is the object of the present invention to enable, during operation, reliable and accurate determination particularly of volumetric flow of the pump and/or the pressure differential over an as large a range of potential operational parameters as possible while also taking account of the viscosity of the fluid to be conveyed.

The object is achieved, using the features of the invention, through an operational method according to patent claim 1. Patent claim 10 relates to a pump or pump arrangement, which pump arrangement is adapted to implement the operational method according to the invention. All method steps in this application, in particular according to patent claims 1 to 11, are implementable in this pump (particularly a blood pump) or pump arrangement. This means that all method features are implementable also in a respective pump/pump arrangement and are to be understood as being disclosed as features of a respective patent claim (for example, as "means plus function" formulation).

In order to avoid repetition, in the following reference is made mainly to the method; this, however, also discloses the device.

Accordingly, the invention relates first of all to a method for operating a fluid pump having a rotor, in particular a blood pump, for conveying fluid, wherein the viscosity of the fluid conveyed, particularly blood, is determined by using measured values of operational parameters of the pump, wherein the pump is operated in a predetermined range of a map of characteristics that links at least two operational parameters of the pump, and wherein in that range at least three operational parameters of the pump are captured and taken account of in order to determine viscosity.

The idea behind the invention is that in a pump of the aforementioned kind it is possible to determine from the data, in selected ranges of the maps of characteristics and given a sufficient number of captured operational parameters, not just volumetric flow and pressure differential across the pump but also the viscosity of the fluid conveyed. This is not possible for all ranges of the maps of characteristics, since in some ranges of the maps of characteristics certain operational parameters can be used for calculation while other parameters are not distinctive or do not allow an unambiguous determination of variables such as volumetric flow and pressure differential across the pump, since in those parameter ranges said variables are not unequivocally dependent on each other. In other ranges of the maps of characteristics, on the other hand, volumetric flow through the pump and pressure differential across the pump can be determined through several parameter combinations, practically making these values over-determined. Thus, given an appropriate choice of captured operational parameters and of the predetermined ranges of the maps of characteristics in which they are captured, also the viscosity of the fluid conveyed can be determined from the measured data.

In an advantageous embodiment of the invention, it is envisaged that the captured operational parameters comprise the rotating speed of a rotor of the pump and/or the motor amperage of the motor driving the rotor and/or a strain of an axial bearing of the rotor. It is here assumed that the pump possesses a rotor with conveying elements for conveying the fluid. It is further assumed that the rotor is driven by means of an electrical motor whose amperage—the motor amperage—is captured. In addition, a bearing strain is measurable, which is a gauge for the axial pressure that the rotor builds, since in an axial pump the rotor, by means of the conveying elements, builds an axially directed propulsive force on the fluid conveyed. The reaction force on the rotor is received in an axial bearing and can be measured there, or it can, for example, also be captured through an axial displacement of the rotor against a progressive counterforce of the bearing.

In a suitable range of a map of characteristics of a pump, these three parameters, for example, are sufficient for determining the viscosity of the fluid. At the same time, motor amperage and/or bearing strain may also be supplemented or replaced by a direct measuring of pressure before or behind the pump at its inlet and/or outlet, possibly in a different range of a map of characteristics, or in a different kind of pump wherein, for example, the bearing is unable to measure axial displacement or wherein there is no axial displacement because of different varieties of bearings being used.

In a further advantageous embodiment of the invention, it is envisaged that the pump is operated in a predetermined range of the map of characteristics linking the rotating speed of the pump rotor and the motor amperage of the pump motor, or of the map of characteristics linking the rotating speed of the pump rotor and the bearing strain of an axial bearing of the pump rotor, wherein in that range the rotating speed of the rotor of the pump as well as motor amperage and the bearing strain of an axial bearing of the rotor are captured and the viscosity is determined therefrom.

In addition, the invention may be advantageously developed by operating the pump in a predetermined range of the map of characteristics linking the volumetric flow of the pump and the pressure differential across the pump, wherein in that range the rotating speed of the rotor of the pump as well as the motor amperage of a motor driving the pump and a bearing strain of an axial bearing of the rotor are captured and the viscosity is determined therefrom.

It may also be advantageously envisaged for the invention that a first value of a volumetric flow through the pump and/or a first value of a pressure differential across the pump is determined from a first group of operational parameters captured in the predetermined range of the map of characteristics, that a second value of a volumetric flow through the pump and/or a second value of a pressure differential across the pump is determined from a second group of operational parameters captured in the predetermined range of the map of characteristics, and that by comparing the first and second values, and in particular from the difference between, or a quotient of first and second values, viscosity is determined. In that case, the values of the pressure differential and the volumetric flow of the pump, which are needed anyway and which after comparing them to physiological values of a patient may also be suitably controlled, are first determined. These quantities are determined in two ways using different parameter combinations, and from a difference the viscosity of the fluid, for example of the blood, is determined. Once the viscosity has been determined, the determined values of the pressure differential and volumetric flow can be corrected.

Additionally, it may advantageously be envisaged that in controlling the pump, several, at least two, maps of characteristics for different viscosities of the fluid to be conveyed, represented by stored value-tuples or parameters, or a map of characteristics containing the viscosity as an additional parameter are used. Thereby, after determining the viscosity, the pump can be controlled with high reliability using the map of characteristics or an interpolation of characteristics of the map of characteristics.

It may also advantageously be envisaged that the axial force of an axial bearing of the pump rotor is captured by capturing an amperage activating an electromagnet of the magnetic axial bearing, or another electrical quantity representing the force generated in the magnetic bearing. The axial position of the rotor then remains practically independent of the axial force while the amperage and/or the bearing strain rises in unison with an increasing axial force for generating the reaction force on the rotor.

In a further advantageous embodiment of the invention, it may be envisaged that the absolute pressure of the fluid is measured at an inlet of the pump and/or at an outlet of the pump by means of a pressure sensor and used as an operational parameter for determining viscosity. Here, even measuring only a single pressure value will yield an evaluable parameter. If pressure is measured at both sides of the pump, a pressure differential can be determined directly and can be compared to a pressure differential expected from the rest of the measurements.

In a further embodiment of the invention it may be envisaged that the pump successively targets two or more points in the map of characteristics within the predetermined range of the map of characteristics, the operational parameters captured at the different points then being linked to each other and considered for determining viscosity. Herein, discrete points in the map of characteristics may be targeted, or particular paths within the map of characteristics may be followed.

Additionally, it may be envisaged that at least one number indexing the composition of the fluid, in the case of blood particularly the hematocrit level, is determined from the respective determined viscosity, particularly while factoring in additional parameters, in particular the temperature.

The viscosity of the fluid is usually linked to environmental parameters as well as to the nature of the fluid. If the environmental parameters such as pressure and temperature are measured, the composition or nature of the fluid can be deduced.

It may additionally be envisaged that the motor amperage and/or the bearing strain of the pump motor is monitored with regard to the speed of changes and that a signal is given when a predetermined threshold is crossed. Thus, if for example a fast or sudden increase or decrease in motor amperage or bearing strain occurs wherein the time derivative exceeds a certain value or wherein predetermined absolute or percentage changes are exceeded within a certain time frame, a malfunction in the pump, conditioned by a pump element or a change in the nature of the fluid, is deduced and a signal is given.

The invention relates, besides a method of the above-described kind, also to a pump arrangement with a pump having a rotor, in particular a blood pump, for conveying fluid, with a storage arrangement storing at least one map of characteristics by means of parameters determining the characteristics and/or by means of a plurality of points in the map of characteristics, the map of characteristics linking the rotating speed of the pump rotor to the motor amperage of the pump motor or linking the rotating speed of the pump rotor to the bearing strain of an axial bearing of the pump rotor, with an arrangement for capturing the rotating speed of the pump rotor, an arrangement for capturing the motor amperage of a motor driving the rotor, and with an arrangement for capturing the bearing strain of a bearing holding the pump rotor, with a control arrangement that adjusts an operation of the pump within a predetermined range, stored in the storage arrangement, of a map of characteristics, and with a determining arrangement that determines, from the captured quantities, a viscosity of the fluid conveyed, provided that operation of the pump takes place within the predetermined range, stored in the storage arrangement, of the map of characteristics.

In a pump of the aforementioned kind, a plurality of separate methods for determining volumetric flow through the pump and, in particular, pressure differential across the pump may in fact be used (alternatively or cumulatively) during operation and independently of determining viscosity. Here, the values of operational parameters of the pump are split up such that for particular values of selected operational parameters a first method for determining volumetric flow and particularly pressure differential is used, and that for other values of operational parameters another method, distinguished therefrom, for determining volumetric flow and particularly pressure differential using an additional operational parameter is used. Thus, there is a split-up of the map of characteristics of the pump according to particular values of the operational parameters, wherein different determining methods may be used for different ranges of the map of characteristics. By proceeding thus, the most sensitive method, or the method for which the respective needed values of the operational parameters can be captured most easily, may for example be used for each range of the map of characteristics, taking into account different sets of operational parameters, which may overlap. Once the current viscosity of the fluid has been determined, the maps of characteristics may then accordingly be applied or be adapted/modified so that control algorithms are used that are suited to the respective viscosity.

It is also conceivable to use, in further ranges of the map of characteristics, additional methods using still other operational parameters than the aforementioned methods.

Additionally, it may be envisaged to simultaneously employ multiple methods in certain ranges of the map of characteristics in order to harmonize the values thus determined, which may occasionally differ from each other, and thereby minimize capture and calculation errors.

In a particular embodiment of the invention it may be envisaged to exclusively use the rotating speed of the pump and the axial force on the pump rotor as the operational parameters considered for determining the volumetric flow through the pump.

In a particular configuration, the temperature of the fluid conveyed may additionally be used for viscosity determination since it has an influence on the viscosity of the fluid, particularly of blood. Temperature measurements may, in controlling the pump, be monitored as a parameter and evaluated also after viscosity has been determined.

Thus in principle, when determining viscosity, more operational parameters are captured than would be necessary for determining volumetric flow through the pump and/or pressure differential in a particular range of the map of characteristics. Through this versatile selection of captured operational parameters in map-of-characteristics determination, it becomes possible to employ different determining methods each according to the range of the map of characteristics in which the current operational state of the pump is situated.

In the following, the invention is presented in the figures of a drawing and subsequently explained by means of exemplary embodiments. There is shown in FIG. 1 schematically, a view of a patient's body with the heart of the patient and a VAD (ventricular assist device) pump, FIG. 2 an axial rotor pump, schematically in a three-dimensional view, FIG. 3 in a schematic side view, the housing of an axial pump with a rotor, a drive, and a magnetic axial bearing, FIG. 4 a typical map of characteristics of a pump with characteristics that enable the attribution of a rotating speed and a pressure differential to a volumetric flow, FIG. 5 a diagram according to FIG. 4 that explains the determination of pressure differential across the pump by means of two different methods, and the comparing of the results, and FIG. 6 schematically, the construction of a pump arrangement for using the method according to the invention.

FIG. 1 shows the torso of a patient 1 with the patient's heart 2 and part of the aorta 3. An inlet port 5 of a VAD pump (ventricular assist device) 6 is connected to a ventricle 4 of the heart, the VAD pump sucking blood from the ventricle 4 in the direction of the arrow 7 to the inlet of the pump and conveying it from the outlet of the pump via the outlet cannula 8 directly into the aorta 3.

Such pumps can substantially support the pumping function of a heart that is ailing or not able to perform to its full capacity. This may be planned as a temporary or as a permanent therapy. The use of axial rotor pumps, which convey blood inside the pump housing in the axial direction 7 by means of a fast-spinning rotor, has been found to be especially advantageous. Such pumps are usually driven by an electromotive drive in the region of the pump housing, able to be supplied by a carry-along battery or a stationary electrical connection. In order to be able to sufficiently exactly check on the patient's health and the operational state of the pump, it is necessary to determine and track volumetric flow through the pump. To achieve this, various methods are known in principle, which for example involve capturing the rotating speed of the rotor and the pressure differential across the rotor. Determining volumetric flow is also possible by means of the rotating speed of the pump and measuring stationary pressure of the blood to be conveyed by means of an absolute pressure sensor 9 at the pump. Finally, volumetric flow can also be determined by an approach of considering the rotating speed of the pump rotor and the torque affecting the rotor, or the rotating speed of the pump rotor and the bearing strain in an axial bearing of the rotor.

In all these methods, volumetric flow and/or pressure differential across the pump is usually determined, by means of maps of characteristics, from the captured measurements for the operational parameters of: rotating speed of the rotor, pressure differential across the rotor, torque of the rotor, absolute pressure in the region of the pump and/or bearing strain in the axial bearing. By means of the method according to the invention, corresponding measuring and determining methods are performed in predetermined ranges of the maps of characteristics in such a way that, given a sufficient number of captured operational parameters, the viscosity of the fluid conveyed can be determined, which can then be taken into account during further operation, allowing a more exact control of the pump's operation.

Figure 2:
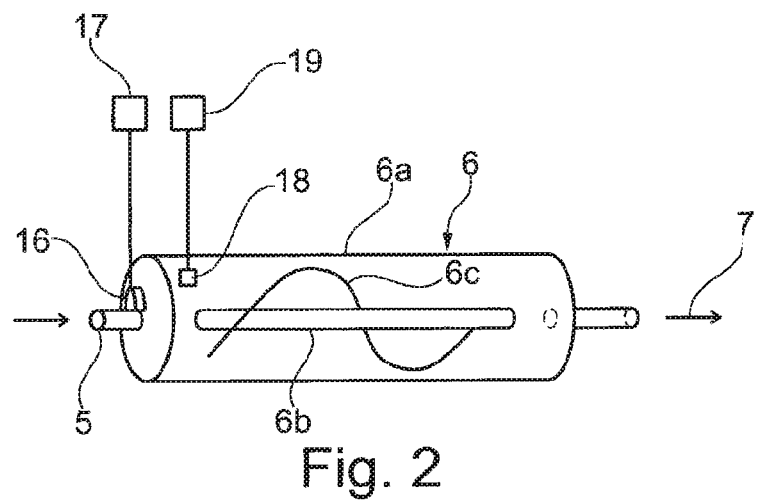
FIG. 2 an axial rotor pump, schematically in a three-dimensional view.

In FIG. 2, an axial pump 6 having a hub 6b mounted in a housing 6a is schematically depicted, one or more conveying elements 6c, for example in the form of a circumferential helical conveying blade, being fixed to the hub. Through rotation of the rotor, the fluid to be conveyed, or the blood, is conveyed in the housing 6a in the direction of the arrow 7. A hub need not be provided if the rotor is mounted in a magnetic axial bearing. In that case, it is merely necessary to shape, arrange and suspend the rotor's conveying elements in a suitable manner.

Figure 3:
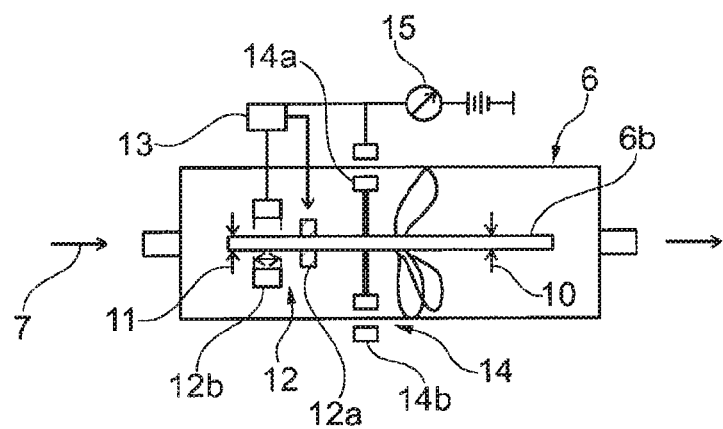
FIG. 3 in a schematic side view, a housing of an axial pump with a rotor, a drive, and a magnetic axial bearing.

In FIG. 3, the mounting and driving of the rotor of the pump 6 is shown in more detail. To begin with, in the region of the hub 6b a first radial bearing is symbolically depicted and designated by the reference sign 10 while a second radial bearing is symbolically depicted in the same manner and is designated by 11. The second radial bearing 11 may for example be combined with a magnetic axial bearing 12, but may also be constructed separately from it.

The axial bearing 12 is configured as an adjustable magnetic axial bearing, wherein a first circular magnet 12a is connected to, and rotates together with, the hub 6b or, if the rotor is configured to be hubless, the rotor.

A second circular magnet or a circular arrangement of individual magnets 12b is arranged stationary in the housing 6a of the pump 6 and surrounds the hub 6b or a part of the rotor. Through repulsion between the stationary magnet 12b or the stationary magnet arrangement 12b on the one hand and the rotating magnet 12a on the hub 6b, an axial force is absorbed that affects the rotor and that opposes, as a reaction force, the flow direction 7 of the fluid through the pump.

The axial bearing 12 comprises a sensor for capturing the axial position of the magnet 12a fixed to the hub, for example with eddy current sensors, the information on the axial position being signaled to a control device 13, for example in the form of a strain measured by the sensors. Thereby, the control loop of the magnetic bearing 12 can be closed, and the control device 13 can adjust the axial position of the magnet 12a and, with that, of the rotor or the hub 6b, to have a constant value. The force that is absorbed by the axial bearing in the process can be determined on the basis of the amperage applied by the control device 13.

With a non-controlled bearing, the force absorbed by the axial bearing may for example be determined, as explained above, by measuring the axial deflection of the hub with respect to the magnetic force of the axial bearing.

In FIG. 3, an electric motor 14 is schematically depicted, which may, for example, provide permanent magnets 14a fixedly connected to the rotor and a stator 14b connected to the pump housing 6a. Thus, a brushless electric motor is implemented through a corresponding control of stator windings. The amperage applied to the stator 14b is detectable by means of a measurement device 15, and from that amperage the generated torque on the rotor can be determined in a simple manner.

Referring back to FIG. 2, it should be noted that a hydrostatic pressure sensor 16, which is connected to a corresponding processing device 17, is depicted there at the pump inlet port 5. A pressure sensor may also be provided at the pump outlet. Thereby a temperature differential across the pump can also be determined directly. In addition, in FIG. 2 a temperature sensor 18, likewise connected to a processing device 19, is depicted within the pump housing 6a. The temperature sensor 18 may also be arranged outside the pump in an area through which the fluid conveyed passes.

Figure 4:
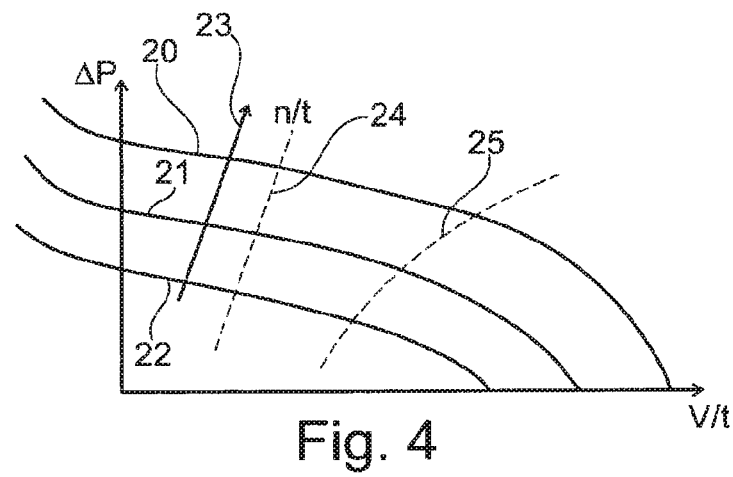
FIG. 4 a typical map of characteristics of a pump with characteristics that enable an attribution of a rotating speed and a pressure differential to a volumetric flow.

FIG. 4 shows a diagram wherein volumetric flow through the pump is plotted on the horizontal axis in volume per time against the pressure differential across the pump for various rotating speeds of the pump. This yields a map of characteristics wherein, as examples, three characteristics 20, 21, 22 are shown that represent different rotating speeds. The arrow 23 thus shows, as a trend, the direction of transition between curves representing different rotating speeds.

Thus, operating points of the pump (pressure differential between pump inlet and outlet and the volumetric flow conveyed through the pump) are represented, in the form of the characteristics, for various rotating speeds of the pump. Here, in order to determine the characteristics, the rotating speed and the axial bearing position of the rotor are recorded as representative quantities for the pressure differential across the rotor. Alternatively, the rotating speed and the torque of the pump motor, measured through the motor amperage, may be captured. By using appropriate regression curves, points of measurement may be interpolated to yield characteristics curves. During operation of the pump, for example the volumetric flow through the pump can thus in each case be determined from the captured operational parameters, for instance from the rotating speed and the axial bearing position of the rotor, in particular regions within the map of characteristics.

Since it was recognized that, for certain types of pumps, there exist regions within the map of characteristics in which the correlation between the bearing position/pressure differential and volumetric flow is not unique or at least is fuzzy when the rotating speed is known, a different method to determine volumetric flow was chosen for certain regions within the map of characteristics. The appropriate determining method can thus be chosen depending on the region within the map of characteristics in which the operating point of the pump is situated, ergo depending, for example, on the rotating speed and/or the pressure differential across the pump. Also when operating the pump according to the stored map of characteristics, the respective appropriate selection of operational parameters is then used for controlling, dependent upon the operational parameters.

For example, in FIG. 4 a partial area of the map of characteristics is formed between the two dotted lines 24 and 25, in which partial map the volumetric flow is not determined from rotating speed and pressure differential across the rotor, or at least not from those parameters alone. In the area between lines 24 and 25, the torque of the rotor, determined by the amperage of the electric drive motor of the rotor, and/or the absolute pressure at the inlet and/or outlet of the pump may for example be considered. These quantities may be evaluated alone or in combination with the rotating speed; however, the bearing position, as indicator for the pressure differential across the rotor, may additionally be considered for the determination of volumetric flow.

In addition, fluid temperature may also be captured by a sensor, since particularly in blood pumps the temperature of the blood has a strong influence on viscosity and therefore on the operational states or parameters of the pump.

Figure 5:
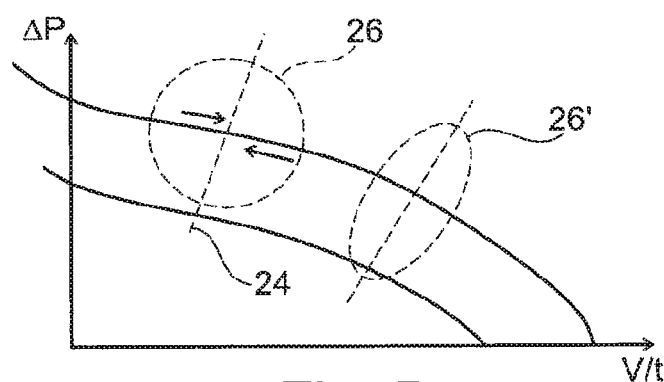
FIG. 5 a diagram according to FIG. 4 that explains the determination of pressure differential across the pump.
Figure 6:
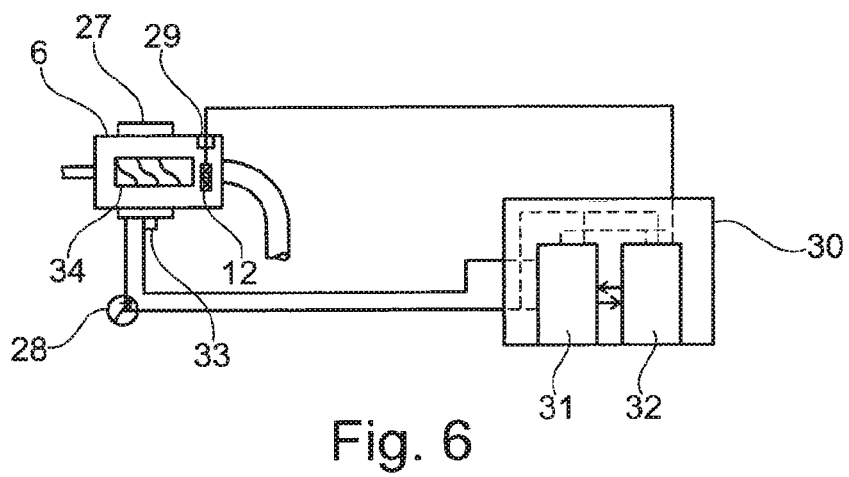
FIG. 6 schematically, a construction of a pump arrangement.

FIG. 5 shows the use of several measuring methods in a particular, predetermined area representing a border area/transition area of the map of characteristics, which shall be indicated here by the dotted circle 26. This area is adjacent to the separating line 24 between the two areas of the map of characteristics that require and allow different measuring methods for determining volumetric flow. In a predetermined area around the separating line 24, several methods for determining volumetric flow and/or pressure differential across the pump can be reliably employed. For example, volumetric flow or pressure differential across the pump can be determined using different captured operational parameters. By comparing the values for volumetric flow and/or pressure differential across the pump that have been determined thus, the viscosity of the fluid conveyed, for example that of the patient's blood, can be determined. In principle, the viscosity can also be determined from the captured redundant operational parameters without concretely determining volumetric flow and/or pressure differential across the pump.

Apart from a method for operating such a pump and for determining volumetric flow in different areas of a map of characteristics, the invention also relates to a method for determining a respective map of characteristics by using different operational parameters in different areas of the map of characteristics.

Moreover, the invention also relates to a pump arrangement comprising respective arrangements for capturing the required operational parameters. Such a pump arrangement is depicted schematically in FIG. 6 and comprises a pump 6 having a rotor 34, a magnetic axial bearing 12, a sensor 29 for the bearing strain, and a motor 27 having an outer stator driving the pump 6. Additionally, a rotating speed sensor 33 and an amperage sensor 28 for the motor amperage are provided. The measured operational parameters are transmitted to an analyzing apparatus 30 comprising a control device 31 with a storage device for characteristics data. Furthermore, the analyzing apparatus 30 comprises a device 32 for determining viscosity, which exchanges data with the control device 31, so that optimized characteristics data can at any one time be used for control of the pump.

Through the invention, determining volumetric flow through a pump using a currently obtained viscosity is significantly improved, especially for such pumps for which a sufficient number of operational parameters are capturable in particular areas of the map of characteristics.

The invention claimed is:

1. A method for operating a fluid pump having a rotor for conveying a fluid, the method comprising:
    operating the fluid pump in a predetermined range of a map of characteristics linking at least two operational parameters of the fluid pump;
    capturing, while the fluid pump is operated in said predetermined range, at least three operational parameters of the fluid pump by measuring, from a plurality of sensors, a plurality of measured values of the at least three operational parameters; and
    determining a viscosity of the fluid conveyed by the fluid pump based on the at least three operational parameters of the fluid pump.

2. The method of claim 1, wherein the captured operational parameters comprise at least one of: a rotating speed of the rotor of the fluid pump, a motor amperage of a motor driving the rotor, or a bearing strain of an axial bearing of the rotor.

3. The method of claim 1, wherein the at least three operational parameters include a rotating speed of the rotor, a motor amperage of a motor of the fluid pump, and a bearing strain of an axial bearing of the rotor, wherein the fluid pump is operated within a predetermined range of the map of characteristics linking the rotating speed of the rotor and the motor amperage of the motor of the fluid pump, or wherein the fluid pump is operated within the predetermined range of the map of characteristics linking the rotating speed of the rotor and the bearing strain of an axial bearing of the rotor, wherein, in said predetermined range, the rotating speed of the rotor of the fluid pump, the motor amperage as well as the bearing strain of the axial bearing of the rotor are captured and the viscosity of the fluid is determined therefrom.

4. The method of claim 1, wherein the at least three operational parameters include a rotating speed of the rotor of the fluid pump, a motor amperage of a motor driving the rotor, and a bearing strain of an axial bearing of the rotor, wherein the fluid pump is operated within a predetermined range of the map of characteristics linking the volumetric flow of the pump and a pressure differential across the fluid pump, wherein, in said range, the rotating speed of the rotor of the fluid pump, the motor amperage of the motor driving the rotor, and the bearing strain of the axial bearing of the rotor are captured, the volumetric flow and the pressure differential are determined from the map of characteristics and/or directly from the measured values, and the viscosity is determined from the volumetric flow and the pressure differential.

5. The method of claim 1, comprising determining a first value of a volumetric flow through the fluid pump and/or a first value of a pressure differential across the fluid pump is from a first group of operational parameters captured in the predetermined range of the map of characteristics; determining a second value of a volumetric flow through the fluid pump and/or a second value of a pressure differential across the fluid pump from a second group of operational parameters captured within the predetermined range of the map of characteristics; and determining the viscosity by comparing the first and second values.

6. The method of claim 1, wherein in controlling the fluid pump, separate maps of characteristics represented by stored value-tuples and/or parameters are used for different corresponding viscosities of the fluid to be conveyed, or a map of characteristics is used that includes the viscosity as an additional parameter.

7. The method of claim 1, wherein the at least two operational parameters include an axial force of a magnetic axial bearing of the rotor, and wherein the at least three operational parameters include at least one of an amperage exciting an electromagnet of the magnetic axial bearing or another quantity representing the force generated in the magnetic axial bearing.

8. The method of claim 1, wherein the at least three operational parameters include an absolute pressure of the fluid, wherein the sensors include a pressure sensor, wherein measuring the measured values includes measuring the absolute pressure at an inlet of the fluid pump and/or at an outlet of the fluid pump by the pressure sensor.

9. The method for operating a fluid pump of claim 1, wherein the fluid pump successively targets two or more points in the map of characteristics within the predetermined range of the map of characteristics, wherein the operational parameters captured at the different points are linked to each other and considered for determining the viscosity.

10. The method of claim 1, wherein at least one number indexing a composition of the fluid is determined from the respective determined viscosity.

11. The method of claim 10, wherein the fluid includes blood and the at least one number indexing the composition of the fluid includes a hematocrit level.

12. The method of claim 10, wherein the at least one number indexing the composition of the fluid is determined from the respective determined viscosity while considering at least one additional parameter including a temperature.

13. The method of claim 12, wherein the at least one additional parameter includes a temperature.

14. The method of claim 1, wherein the at least three operational parameters include a motor amperage and/or a bearing strain, the method further comprising monitoring the motor amperage and/or the bearing strain with regard to the speed of changes; and providing a signal in response to the motor amperage and/or the bearing strain crossing a predetermined threshold.

15. The method of claim 1, wherein the fluid includes blood.

16. A method for operating a fluid pump having a rotor for conveying a fluid, the method comprising:
operating the fluid pump in a predetermined range of a map of characteristics linking at least two operational parameters of the fluid pump;
capturing, while the fluid pump is operated in said predetermined range, at least three operational parameters of the fluid pump by measuring, from a plurality of sensors, a plurality of measured values of the at least three operational parameters, wherein the at least two operational parameters are included in, and/or determined from, the measured values of the at least three operational parameters; and
determining a viscosity of the fluid conveyed by the fluid pump as:
the viscosity linked to one or more of the at least two operational parameters in the map of characteristics, or
a difference between, or a quotient of, a pressure differential and a volumetric flow, wherein the pressure differential and/or the volumetric flow is and/or are determined from the map of characteristics.

\* \* \* \* \*